(12) United States Patent
Bruggeman et al.

(10) Patent No.: US 11,337,441 B2
(45) Date of Patent: May 24, 2022

(54) PROBIOTIC COMPOSITION FOR USE IN A FEED ADDITIVE

(71) Applicant: NUTRITION SCIENCES N.V., Drongen (BE)

(72) Inventors: Geert Bruggeman, Bruges (BE); Johan Rietberg, Drongen (BE); Roland Brugger, Ghent (BE)

(73) Assignee: NUTRITION SCIENCES N.V., Drongen (BE)

( * ) Notice: Subject to any disclaimer, the term of this patent is extended or adjusted under 35 U.S.C. 154(b) by 0 days.

(21) Appl. No.: 16/978,083

(22) PCT Filed: Mar. 6, 2019

(86) PCT No.: PCT/EP2019/055612
§ 371 (c)(1),
(2) Date: Sep. 3, 2020

(87) PCT Pub. No.: WO2019/170774
PCT Pub. Date: Sep. 12, 2019

(65) Prior Publication Data
US 2021/0204565 A1    Jul. 8, 2021

(30) Foreign Application Priority Data

Mar. 7, 2018   (BE) .................................. 2018/5139

(51) Int. Cl.
*A61K 35/747*     (2015.01)
*A61K 35/00*      (2006.01)
*A23K 10/18*      (2016.01)
*C12N 1/20*       (2006.01)
*C12R 1/225*      (2006.01)

(52) U.S. Cl.
CPC ............ *A23K 10/18* (2016.05); *A61K 35/747* (2013.01); *A61K 2035/115* (2013.01); *C12N 1/205* (2021.05); *C12R 2001/225* (2021.05)

(58) Field of Classification Search
None
See application file for complete search history.

(56) References Cited

U.S. PATENT DOCUMENTS

2017/0202890 A1    7/2017   Yonejima et al.

FOREIGN PATENT DOCUMENTS

| KR | 10-2006-0006342 | 1/2006 |
| KR | 10-2013-0084443 | 7/2013 |

OTHER PUBLICATIONS

Kikuta et al. JP 2004329056 A, abstract, pp. 1-2, 2004.*
International Search Report dated Apr. 30, 2019 in corresponding International (PCT) Patent Application No. PCT/EP2019/055612.
Database WPI, Week 200673, Thomson Scientific, AN 2006-704407, XP002782913.
Database WPI, Week 201379, Thomson Scientific, AN 2013-M47533, XP002782914.

* cited by examiner

*Primary Examiner* — Sarvamangala Devi
(74) *Attorney, Agent, or Firm* — Wenderoth, Lind & Ponack, L.L.P.

(57) ABSTRACT

The current invention concerns a feed additive comprising a bacterial culture or a processed bacterial culture and a method for enhancing the zootechnical performance of animals. The bacterial culture comprises an isolated lactic acid bacterium strain, wherein that strain comprises a 16S rRNA sequence exhibiting at least 95% sequence identity to SEQ ID N° 1.

6 Claims, No Drawings
Specification includes a Sequence Listing.

SEQUENCE LISTING

<160> NUMBER OF SEQ ID NOS: 1

<210> SEQ ID NO 1
<211> LENGTH: 805
<212> TYPE: DNA
<213> ORGANISM: Lactobacillus sp. LMG 28117

<400> SEQUENCE: 1

```
gacgaacgct ggcggcatgc ctaatacatg caagtcgaac gagcttccgt tgaatgacgt    60
gcttgcactg atttcaacaa tgaagcgagt ggcgaactgg tgagtaacac gtgggraatc   120
tgcccagaag caggggataa cacttggaaa caggtgctaa taccgtataa caacaaaatc   180
cgcatggatt ttgtttgaaa ggtggcttcg gctatcactt ctggatgatc ccgcggcgta   240
ttagttagtt ggtgaggtaa aggcccacca agacgatgat acgtagccga cctgagaggg   300
taatcggcca cattgggact gagacacggc ccaaactcct acgggaggca gcagtaggga   360
atcttccaca atggacgaaa gtctgatgga gcaatgccgc gtgagtgaag aagggtttcg   420
gctcgtaaaa ctctgttgtt aaagaagaac acctttgaga gtaactgttc aagggttgac   480
ggtatttaac cagaaagcca cggctaacta cgtgccagca gccgcggtaa tacgtaggtg   540
gcaagcgttg tccggattta ttgggcgtaa agcgagcgca ggcggttttt taagtctgat   600
gtgaaagcct tcggcttaac cggagaagtg catcggaaac tgggagactt gagtgcagaa   660
gaggacagtg gaactccatg tgtagcggtg gaatgcgtag atatatggaa gaacaccagt   720
ggcgaaggcg gctgtctagt ctgtaactga cgctgaggct cgaaagcatg ggtagcgaac   780
aggattagat accctggtag tccat                                         805
```

PROBIOTIC COMPOSITION FOR USE IN A FEED ADDITIVE

A sequence listing in electronic (ASCII text file) format is filed with this application and incorporated herein by reference. The name of the ASCII text file is "2020-2252A-REPLACEMENT SEQUENCE LISTING.txt"; the file was created on Jan. 29, 2021; the size of the file is 1 KB.

TECHNICAL FIELD

The invention is directed to bacterial cultures and their use as feed additives, preferably in animal feed.

BACKGROUND

In order to reduce the occurrence of pathogenic organisms in animal production, antibiotics are often added in low doses. The problem of resistance development of pathogenic organisms and the transfer of the antibiotic substances into animal foodstuffs makes it very desirable to reduce the use of antibiotics to animals as well as humans.

Certain microorganisms, e.g. different lactic acid bacteria, have a favorable effect on the gastrointestinal flora of animals, including humans. Consumption of a probiotic product by a host is intended to positively affect the metabolic processes taking place in the host's gastrointestinal tract and therefore to reduce disorders and to increase the food utilization. The favorable microorganisms reduce disturbances from pathogenic microorganisms by suppressing the undesired organisms in different ways. Additionally, these microorganisms often contribute to food digestion through fermentation, resulting in a more effective utilization of nutrients.

The two major genera of microorganisms commonly associated with probiotic activity include Lactobacillus sp. and Bifidobacteria sp. The beneficial effects attributed to probiotics include increased resistance to infectious diseases, healthier immune systems, reduction in irritable bowel syndrome, reductions in blood pressure, reduced serum cholesterol, milder allergies and tumor regression. Nevertheless, the claimed beneficial qualities of specific bacterial strains are seldom proven.

US2017202890 discloses a *lactobacillus* strain that improves hyperuricemia, fatty liver and lifestyle related diseases. US2017202890 is however not directed to a use in feed or cattle. The same goes for KR20060006342 and KR2013008443 which fail to disclose a use in feed.

Therefore, there remains a need in the art for new lactic acid bacterial strains that exhibit probiotic activities. Particularly, there is a need for more lactic acid bacterial strains that have the proven capacity to improve the zootechnical performance of animals. In second instance, there is also need for a composition that can positively influence the gastrointestinal flora and/or the gastrointestinal histology of animals.

The present invention aims to resolve at least some of the problems mentioned above.

SUMMARY OF THE INVENTION

The invention thereto aims to provide a method for improving the zootechnical performance of animals according to claim 1. More in particular, the invention provides a feed additive comprising a bacterial culture or a processed bacterial culture, wherein said culture comprises an isolated lactic acid bacterium strain, characterized in that the strain comprises a 16S rRNA sequence exhibiting at least 95% sequence identity to SEQ ID N° 1. This strain is able to survive and colonize the gastrointestinal tract of an animal and has probiotic properties which are beneficial for animal health, resulting amongst others in a decreased need for antibiotic treatment of animals, an increase in daily weight gain and a decrease in daily feed intake which constitute serious economic advantages.

In a further aspect, the present invention provides a feed additive according to claim and an animal feed according to claim 19.

In a third aspect, the present invention provides a use according to claim 21. More in particular, the invention provides a method for positively enhancing the zootechnical performance of animals comprising the step of providing said animals with a feed additive or an animal feed according to the current invention.

Administration of the probiotic strain is thought to improvement the gastrointestinal flora of the animals therefore prevents its colonization by harmful micro-organisms. Therefore, the invention further helps prevent the upcoming spread of drug resistant enteric pathogens. The positive effects of the bacterial strain in the animal are further reflected by an increase in animal welfare, a decrease in gastrointestinal disease incidence and a decrease in animal mortality rate. In addition the bacterial strain according to the invention promotes efficient digestion and nutrient adsorption, thus providing for animals that require less feed.

DETAILED DESCRIPTION OF THE INVENTION

The present invention concerns a novel feed additive and a novel animal feed comprising a probiotic lactic acid bacterium culture or a processed bacterial culture bacterial culture comprising a novel and the use thereof to improve the zootechnical performance of animals.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

The term "culture" as used herein refers to a population of microorganisms that are propagated on or in media of various kinds.

The term "sequence identity" as used herein, refers to the extent that sequences are identical on a nucleotide-by-nucleotide bases over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. Determining the percentage of sequence identity can be done manually, or by making use of computer programs that are available in the art.

In microbiology, "16S rRNA sequence" refers to the sequence derived by characterizing the nucleotides that comprise the 16S ribosomal RNA gene(s).

The term "probiotics" as used here, refers to microorganisms, which when administered in adequate amounts confer health benefits on the host.

The terms "gastrointestinal flora", gut microbiota, gastrointestinal microbiota, gut microflora, gastrointestinal microflora, gut microbiome or gastrointestinal microbiome refer to the complex community of microorganisms that live in the gastrointestinal tracts of animals.

An "animal feed" as used herein comprises the feed as well as the drinking water, and the inhaled air of the animal in question.

The term "colony-forming unit" (CFU) refers to a unit that is used to estimate the number of bacteria, yeast or fungal cells in a sample, that can be for example a cell culture, a feed additive or a feed composition. Although generally only used when referring to viable bacteria, the term colony forming unit, or CFU will also be defined as a single non-viable or non-culturable bacterial cell when referring to embodiments of the present invention composed of a processed bacterial culture.

A "processed bacterial culture" includes an isolated bacterial cell culture treated by concentration, drying, freeze-drying, drum-drying, spray-drying and the like. A processed bacterial culture includes non-viable or non-culturable bacterial cells, disrupted cells, and culture medium comprising those cells or disrupted cells. In addition, a bacterial disrupture product and a homogenate after removal of debris by centrifugation after bacterial disrupture can be used as the processed bacterium of the present invention. A "processed bacterial culture" comprises at least part of the DNA of the bacterial cell, therefore allowing identification of the bacterial strain in the processed bacterial culture.

The term "isolated" means that the strain has been removed from its natural environment. "Isolated" thus implies a purification step. However, "isolated" does not necessarily reflect the extent to which the microorganism has been purified. The strains of the current application are purified at least 2×, at least 5×, at least 10×, at least 50× or at least 100× from the raw material from which it is isolated.

The term "Feed Conversion Ratio" or "FCR" describes the efficiency with which the animals convert feed into the desired output. For dairy cows, for example, the output is milk, whereas in animals raised for meat (such as beef cows, pigs, chickens, and fish) the output is the flesh, that is, the body mass gained by the animal, represented either in the final mass of the animal or the mass of the dressed output. FCR is the mass of the input (feed) divided by the output.

The term "zootechnical performance" can be understood as one or more parameters linked to the animal that has improved and which are important for farm animals, such as cattle, poultry, pigs, horses etc. In particular, zootechnical parameters may include (average) weight, (average) daily weight increase, (average) daily feed consumption, (average) feed conversion ratio etc. According to Art. 6, Reg. EC 1831/2003, a zootechnical feed additive is defined as "any additive used to affect favourably the performance of animals in good health or used to affect favourably the environment".

In a first aspect, the invention provides a novel feed additive comprising a bacterial culture or a processed bacterial culture, wherein said culture comprises an isolated lactic acid bacterium strain, characterized in that the strain comprises a 16S rRNA sequence exhibiting at least 95% sequence identity to SEQ ID N° 1, preferably 99%, more preferably 100% sequence identity to SEQ ID N° 1. Accordingly in a second aspect, the invention provides a novel animal feed comprising such a feed additive.

The invention thereto provides a lactic acid bacterium strain with probiotic properties. More in particular, the invention concerns a bacterial culture comprising an isolated lactic acid bacterium strain, characterized in that the strain comprises a 16S rRNA sequence exhibiting at least 95% sequence identity to SEQ ID N° 1, preferably 99%, more preferably 100% sequence identity to SEQ ID N° 1. This strain is safe for animal consumption, is capable of surviving gastric transit when consumed and is physiologically active in the gastrointestinal tract. In a further embodiment of the invention, the isolated lactic acid bacterium strain was deposited on Jan. 3, 2018 as patent deposit N° LMG P-30455 at 2018 at the Belgian Coordinated Collection of Micro-organisms (BCCM), Laboratorium voor Microbiologie-Bacterienverzameling (LMG).

The inventors have found that the bacterial culture as well as the processed bacterial culture have remarkable positive effects when administered to animals and contribute to an unexpected improvement in the zootechnical performance of these animals. Without wishing to be bound by theory, the zootechnical improvements are thought to be related to an improvement of the gastrointestinal flora which prevents gastrointestinal colonization by harmful micro-organisms thus reducing the need for antibiotic treatment of animals. Therefore, the invention further helps prevent the upcoming spread of drug resistant enteric pathogens. The positive effects of the bacterial strain in the animal are further reflected by an increase in animal welfare, a decrease in gastrointestinal disease incidence and a decrease in animal mortality rate. In addition the bacterial strain according to the invention is thought to promote efficient digestion and nutrient adsorption, thus providing for animals that require less feed. In addition, these animals have a smaller food conversion rate or FCR, which is reflected by an enhanced daily weight gain and a lower daily feed intake, resulting in an enormous economic advantage as the profitability of growing the animals increases considerably, while the food cost decreases.

The bacterial culture comprising the lactic acid bacterium strain can be combined with other bacterial strains. Therefore, in a further embodiment the feed additive further comprises one or more additional bacterial strains such as, but not limited to, lactic acid bacterium strains comprising a 16S rRNA sequence exhibiting less than 95% sequence identity to SEQ ID N° 1, bacterial strains belonging to the phylum Firmicutes and bacterial strains belonging to the genus of *Bacteroides*, which constitute the major groups of gastrointestinal flora population.

As mentioned above, consumption of the referred lactic acid bacterium strain results in remarkable health benefits to the host. Without wishing to be bound by theory, these benefits are thought to be related, at least partially, to the ability of the strain to colonize the host's gastrointestinal or respiratory tract where they compete for nutrients with other microbes including pathogenic ones. In addition the positive improvement of zootechnical performance of the animals might be caused due to the strain's ability to produce substances or metabolites with antimicrobial and/or antipathogenic activity against a wide range of pathogens. Furthermore the novel strain has a positive influence on digestion and nutrient uptake in the gastrointestinal tract of the host.

In order to further stimulate the positive effect of the bacterial strain in the gastrointestinal or respiratory tracts of the host, other components that can serve as substrates for these bacteria can be included in the feed additive. Alternatively, these components can help stabilize the aqueous phase of the feed additive when subsequent freeze-drying or spray-drying of the mixture is desired. Accordingly, in one embodiment of the invention, the feed additive further comprises one or more ingredients selected from the group consisting of carbohydrates, proteins, lipids, water and combinations thereof. In addition, ingredients that are known to further promote animal growth and/or health can also be provided in the feed additive. These ingredients include but are not limited to vitamins, enzymes, trace minerals, electrolytes, essential oil components and amino acid residues.

Lactic acid bacteria are known for their ability to convert carbohydrates to lactic acid. Fermentation is believed to contribute to the probiotic effect of the strain of the invention when consumed by the host. In a further embodiment the carbohydrates present in the feed additive are selected from the group consisting of monosaccharides, disaccharides, oligosaccharides, polysaccharides and combinations thereof. Carbohydrates that may be used in accordance to the present invention include, but are not limited to trehalose, maltose, sucrose, dextrose, lactose, inulin, ribose, malt dextrin, starch and the like. In a further preferred embodiment the carbohydrates present in the feed additive are selected from the group consisting of fructose, dextrose, lactose, inulin, maltose, starch and combinations thereof. The inventors have found that these carbohydrates are especially well suited substrates for fermentation by the lactic acid bacterium strain of the invention.

Furthermore, the feed additive according to the invention also includes polypeptides and can further also include proteins and lipids. Proteins suitable to be used in the feed additive according to the invention include whey protein, egg albumin, gelatin, milk proteins, blood plasma proteins, soy proteins, fish meal and other animal and plant proteins. The proteins serve on one hand as a nutrient and nitrogen source for the animal as well as for the lactic acid bacterium strain, and on the other hand can help stabilize the aqueous phase of the feed additive prior to freeze-drying or spray-drying of the mixture. Another nitrogen source suitable for inclusion in the feed additive of the invention includes, but is not limited to peptones, which are a water-soluble mixture of polypeptides and amino acids resulting from partial hydrolysis of proteins. Accordingly, in another embodiment of the invention, the proteins present in the feed additive are selected from the group consisting of whey proteins, milk proteins, blood plasma proteins and combinations thereof. Suitable lipids include, but are not limited to, soy bean oil, olive oil, palm kernel oil, peanut oil, walnut oil, canola oil, coconut oil, fish oil and the like. In another further embodiment, the lipids present in the feed additive are selected from the group consisting of soy bean oil, palm kernel oil, coconut oil, fish oil and combinations thereof. These lipids contribute as energy sources for the animal as well as stabilizers during the aqueous phase of the feed additive prior to freeze-drying or spray-drying.

Other suitable ingredients that can be included in the feed additive according to the invention include but are not limited to fatty acids, non-fermentable oligosaccharides, plant derived biologically active compounds and combinations thereof. Plant derived biologically active compounds as used herein include such compounds as polyphenols, saponins, flavonoids, monoterpenes, allyl sulfides, lycopenes, carotenoids, polyacetylenes, silymarin, glycyrrhizin catechins, antioxidants, and others.

In another further embodiment of the invention, the bacterial culture or processed bacterial culture is present in the feed additive in amount of at least $10^7$ cells per gram based on the total weight of the feed additive, preferably between $10^7$ and $10^9$ cells per gram based on the total weight of the feed additive. The amount of the desired bacterial cells can be determined using various methods known to the skilled person. In the case where the lactic acid bacterial culture has been included in the feed additive as a viable cell culture, for example, cells can be counted directly using a counting chamber or by plating on growth medium and counting the colony forming units (CFU). Alternatively, several methods for automated cell counting are known in the art which can be used to determine the amount of cells in the feed additive according to the present invention, including for example flow cytometry. In the case where cells might have been disturbed by processing of the bacterial culture prior to inclusion in the feed additive, the cell count can be performed based on PCR-based quantification of the specific 16S rRNA sequence corresponding to the strain present in the feed additive. These PCR-based methods are known to the person skilled in the art and include, but are not limited to, Real-Time PCR (RT-PCR) and quantitative PCR (qPCR). It goes without saying that other methods known in the art suited for the quantification of bacterial cultures or processed bacterial cultures may likewise be applied in combination with the current invention.

The bacterial culture or processed bacterial culture according to the current invention is provided in the feed additive as powder (a dried lactic acid bacterium culture), as a liquid preparation or as a paste. When provided as a dried composition, the feed additive ingredients including the lactic acid bacterial culture are freeze-dried, air dried, drum dried or spray-dried using standard methods known to the skilled person. Preferably, the bacterial strain is present in the feed additive as a powder, a pellet, a granule, a paste or a liquid. In a further embodiment of the invention, the lactic acid bacterial culture or processed bacterial culture is provided in the feed additive as a spray-dried powder. Spray-drying is a method of producing a dry powder from a liquid or slurry by rapidly drying with a hot gas. Preferably, the lactic acid bacterial culture is mixed with a suitable carrier prior to spray-drying. Spray drying is particularly well suited for drying a bacterial culture or processed bacterial culture as it can be used not only to dry but also to simultaneously encapsulate the culture particles in a suitable carrier. Alternatively, the lactic acid bacterial culture or processed bacterial culture can also be provided as a dry powder or solid in the feed additive using a freeze dryer (lyophilizer), a drum dryer or a pulse combustion drier.

In another further embodiment the feed additive is in the form of a liquid preparation or a solid preparation, such as but not limited to a gelatin capsule filled with a dried lactic acid bacterium composition. Alternatively, the feed additive can be provided in the feed in the form of a liquid preparation which is used to coat the feed particles, for example, but not restricted to, using vacuum coating of feed granules.

In another embodiment the feed additive is provided directly to the animal in the form of a bolus taken orally such as, but not limited to, a gelatin capsule, a pressed tablet, a gel cap or as a liquid beverage. In another embodiment the feed additive according to the present invention is provided to the animal through addition of the feed additive comprising the bacterial culture to the animal feed, where "animal feed" as used herein comprises the feed as well as the drinking water of the animal.

In another further embodiment, the feed additive is provided through nasal administration and/or inhalation. Aerosols for inhalation can be generated by nebulizing the feed additive. As used herein, the term "aerosol" is used in its conventional sense as referring to very fine liquid or solid particles carried by a propellant gas under pressure. The feed additive formulated for delivery to the respiratory tract can further comprise a pharmaceutically acceptable carrier. Such formulations are generally solutions, e.g. aqueous solutions, ethanolic solutions, aqueous/ethanolic solutions, saline solutions and colloidal suspensions. Any method known to the skilled person that is useful in the generation of aerosols can be used in the present invention. The aerosol according to the invention can further comprise a fluid carrier and/or a propellant. The aerosol can be in the form of a solution, suspension, emulsion, powder, or semi-solid preparation. Aerosols employed in the present invention are intended for administration as fine, solid particles or as liquid mists via the respiratory tract of an animal. Various types of propellants known to one of skill in the art can be utilized. Examples of suitable propellants include, but is not limited to, hydrocarbons or other suitable gases. The feed additive can also be provided through nasal administration or inhalation using a nebulizer, which is an instrument that generates very fine liquid particles of substantially uniform size in a gas. Preferably, a liquid containing the feed additive is dispersed as droplets. The resulting mist penetrates into the respiratory tract of the animal upon inhalation. Alternatively, the feed additive can be administered as a powder for inhalation.

In another further embodiment of the invention the lactic acid bacterial culture or processed bacterial culture is present in the animal feed in an amount of at least $10^4$ cells per gram based on the total weight of the animal feed, preferably between $10^4$ and $10^6$ cells per gram. The feed additive according to the current invention is present in the animal feed as a meal, a pellet, a paste or a liquid.

The inventors have found that consumption of the bacterial culture or processed bacterial culture of the invention by an animal results in an unexpected improvement of the gastrointestinal flora, the histology and/or the zootechnical performance of the host animal. Therefore, and in a fourth aspect, the invention provides a method for positively enhancing the gastrointestinal flora, the gastrointestinal histology and/or the zootechnical performance of animals comprising the step of providing said animals with a feed additive or an animal feed according to the invention, preferably the feed additive or the feed is administered to the animals as a liquid or as a powder. This improvement promotes more efficient digestion and faster growth of the animals. In addition, the method of the invention results in healthier animals that are less prone to gastrointestinal diseases and thus show a decrease in mortality rate. Finally, the method of the invention also has the advantage that the need for administering antibiotics to the animals is decreased.

Because in principle all animals are colonized by microbial strains, the method described is suited for all animals. Nevertheless, some specificity is known to occur in the host-bacteria interaction. Therefore, in one embodiment, animals for which the method according to the invention is suited are selected from the group consisting of mammals, fish, crustaceans and birds. Mammals for which the method is suited include, but are not limited to humans, horses, donkeys, dogs, cats, deer, rabbits, sheep, goats, pigs and cows, preferably humans, horses, dogs, cats, rabbits, sheep, pigs and cows. Fish species for which the method of the invention is suited include, but are not limited to freshwater fish such as Salmonidae, fish belonging to the Tilapiini cichlid tripe generally known as Tilapia, fish belonging to the genus Pangasius, catfish, European carp, Amur carp varieties generally known as Koi, northern pike, and trout, more preferably Samonidae, Tilapia and Pangasius. Crustacea for which the method is suited include, but are not limited to shrimps, crabs, lobsters and krill, preferably shrimps. Bird species for which the method of the invention is suited include, but are not limited to chickens, turkeys, geese and ducks, preferably chickens and turkeys.

Without wishing to be bound by theory, it is thought that providing animals with the probiotic feed additive according to the current invention results in attachment of the probiotic bacteria to the gastrointestinal or respiratory mucosa, colonization of the gastrointestinal or respiratory tract and thereby prevention of attachment of harmful micro-organisms thereon. The positive enhancement of the gastrointestinal flora in an animal is reflected accordingly by an increased number of beneficial bacteria in the gastrointestinal tract compared to the number of detrimental bacteria. More specifically, the method of the invention can be used to enhance the existence of beneficial bacterial strains in the gastrointestinal tract (i.e. the gastrointestinal flora). Non-limiting examples of beneficial bacterial cultures are bacterial strains belonging to the phylum Firmicutes and bacterial strains belonging to the genus of *Bacteroides*.

The method of the invention is thought to result in a healthier, more balanced gastrointestinal flora, eventually resulting in the amelioration of animal welfare. Positive enhancement of the gastrointestinal flora of an animal is a way to combat pathogenic bacteria in the gastrointestinal tract as the beneficial bacteria limit the growth of harmful bacteria. Therefore, the method according to the invention is thought to lead to a significant reduction in the need for antibiotic treatment of animals. This contributes to further preventing the upcoming spread of drug resistant enteric pathogens.

The health of the gastrointestinal tract can be evaluated based on the histological properties of the large intestine or of the small intestine. The small intestine or small bowel is the part of the gastrointestinal tract between the stomach and the large intestine, and is where most of the end absorption of food takes place. The epithelial component of the small intestine is composed of villi (finger like projections) and crypts of Liberkuhn (crypts). The ratio of villus length to crypt length is characteristic for the health status of the animal and lies within fixed values which are known to the person skilled in the art. Positive enhancement of the gastrointestinal histology in an animal as a result of the method described by the current invention can thus be evaluated by measuring the ratio of villus length over crypt length. Positively enhanced gastrointestinal histology resulting from the method of the invention leads to a better adsorption of nutrients in the intestine. Therefore, the method according to the invention results in animals that need less feed, thus a concomitant lower feed cost can be achieved.

Finally, the method according to the invention results in a positive enhancement in the zootechnical performance of the animals in question. While not wishing to be bound by theory, it is believed that the positively enhanced gastrointestinal flora and/or the positively enhanced gastrointestinal histology results in more efficient nutrient uptake and nutrient utilization in the animal. This is eventually reflected by the positively enhanced zootechnical performance of the animal. An improvement in the zootechnical performance of an animal correlates with an enhanced daily weight gain and a lower daily feed intake, resulting in an enormous economic advantage as the profitability of growing the animals increases considerably.

In one embodiment of the method, the animal is provided of a single daily dose of feed additive comprising the bacterial culture according to the current invention. In another embodiment of the method, the animal is provided of multiple daily doses of feed additive comprising the bacterial culture according to the current invention. The total amount consumed will depend on the individual needs of the animal and the weight and size of the animal. The preferred dosage for any given application can be easily determined by titration. Titration is accomplished by preparing a series of standard weight doses each containing from approximately $10^4$ to $10^9$ lactic acid bacterial cells per gram. A series of doses are administered beginning at 0.5 grams and continuing up to a logical endpoint determined by the size of the animal and the dose form. The appropriate dose is reached when the minimal amount of lactic acid bacteria composition required to achieve the desired results is administered. The appropriate dose is also known to those skilled in the art as an "effective amount" of the probiotic compositions of the present invention.

Finally, as described above, feeding an animal with the novel bacterial strain in the form of a feed additive or an animal feed as described above can be efficiently used to positively enhance the zootechnical performance of animals. Therefore, in a fifth and final aspect, the invention provides the use of a feed additive or an animal feed as described above for positively enhancing the zootechnical performance of animals. Zootechnical parameters that are improved include feed conversion ratio, weight, daily weight increase, overall animal health, daily feed consumption etc.

In an embodiment, said feed additive serves as a digestibility enhancer and/or gut flora stabilizer or enhancer.

In an embodiment, said feed additive improves the zootechnical performance of young animals, e.g. from birth to a stage prior to adulthood, such as piglets, calves or broilers.

The invention is further described by the following non-limiting examples which further illustrate the invention, and are not intended to, nor should they be interpreted to, limit the scope of the invention.

The present invention will be now described in more details, referring to examples that are not limitative.

EXAMPLES

Example 1: Zootechnical Performance of Piglets Fed with a Feed Additive According to an Embodiment of the Invention The study included a total of 45 piglets, about three weeks old and weaned at 21 days. These animals were divided into three groups, each comprising 15 piglets. Piglets belonging to "Group 1" were fed daily with a standard piglet feed. Piglets belonging to "Group 2" were fed daily with a standard piglet feed supplemented with 0.1% (based on the total weight of the feed) of a feed additive comprising $10^7$ cells/gram (based on the total weight of the additive) of the lactic acid bacterial culture according to an embodiment of the invention. Piglets belonging to "Group 3" were fed daily with a standard piglet feed supplemented with 0.1% (based on the total weight of the feed) of a feed additive comprising $10^7$ cells/gram (based on the total weight of the additive) of the processed lactic acid bacterial culture according to an embodiment of the invention. The piglets were further provided with drinking water ad libitum.

Note that the term "colony-forming unit" (CFU), although generally only used when referring to viable bacteria, is also used to describe a single non-viable bacterial cell when referring to embodiments of the present invention composed of a processed bacterial culture. The processed lactic acid bacterial culture of this example includes an isolated bacterial cell culture treated by spray-drying and comprises non-viable bacterial cells, disrupted cells, and culture medium comprising those cells or disrupted cells.

The animals were separated by group and contained in isolated pens. The experiment was conducted for a duration of 6 weeks. Body weight measurements were performed before the start of the trial, 2 weeks after and 4 weeks after the start of the trial.

The results of the trial are shown in Table 1 for 5 week old piglets, and in Table 2 for 9 week old piglets.

As shown in Tables 1 and 2, feeding piglets with the animal feed according to an embodiment of the invention resulted in a positive improvement in daily growth, without the need for a higher daily feed intake. Accordingly, the food conversion rate (FCR) of the piglets was lower when the piglets were fed with a feed according to an embodiment of the invention. Providing the animals with an animal feed according to an embodiment of the invention not only resulted in the positive enhancement in the zootechnical performance of the animals but also in an enhancement in animal welfare as is illustrated by the decrease in mortality of animals provided with the animal feed according to an embodiment of the invention.

TABLE 1

Zootechnical performance of 5-week old piglets.

|  | GROUP 1 | GROUP 2 | GROUP 3 |
|---|---|---|---|
| START WEIGHT (kg) | 5.63 | 5.34 | 5.50 |
| END WEIGHT (kg) | 8.13 | 7.88 | 8.08 |
| FEED NTAKE (g/day) | 254 | 252 | 245 |
| DAILY GROWTH (g/day) | 179 | 182 | 184 |
| FOOD CONVERSION RATE (FCR) | 1.42 | 1.39 | 1.33 |
| MORTALITY (%) | 6.7 | 0.0 | 0.0 |

TABLE 2

Zootechnical performance of 9-week old piglets.

|  | GROUP 1 | GROUP 2 | GROUP 3 |
|---|---|---|---|
| START WEIGHT (kg) | 5.63 | 5.34 | 5.50 |
| END WEIGHT (kg) | 22.53 | 22.90 | 22.85 |
| FEED INTAKE (g/day) | 542 | 551 | 545 |
| DAILY GROWTH (g/day) | 345 | 358 | 354 |
| FOOD CONVERSION RATE (FCR) | 1.57 | 1.54 | 1.54 |
| MORTALITY (%) | 13.3 | 6.7 | 0.0 |

It is supposed that the present invention is not restricted to any form of realization described previously and that some modifications can be added to the presented example without reappraisal of the appended claims. For example, the present invention has been described referring to piglets, but it is clear that the invention can be applied to calves for instance or to broilers.

The invention claimed is:

1. A method of positively enhancing the zootechnical performance of animals and/or the feed conversion ratio, the method comprising:
   providing said animals with an effective amount of a feed additive or a feed supplement with said feed additive,
   wherein said feed additive comprises the isolated lactic acid bacterium strain deposited as LMG P-30455.

2. The method of claim 1, wherein the amount of said lactic acid bacterium strain is at least $10^7$ cells per gram based on the total weight of the feed additive.

3. The method of claim 1, wherein said lactic acid bacterium strain is present as a powder, a pellet, a granule, a paste or a liquid.

4. The method of claim 1, wherein said lactic acid bacterium strain is provided in the feed additive as a spray-dried powder.

5. The method according to claim 1, wherein said feed additive is in the form of a solid preparation or a liquid preparation.

6. The method according to claim 1, wherein said animals are selected from the group consisting of mammals, fish, crustacean and birds.

* * * * *